(12) United States Patent
Masters et al.

(10) Patent No.: US 8,623,393 B2
(45) Date of Patent: Jan. 7, 2014

(54) BIOMATRIX STRUCTURAL CONTAINMENT AND FIXATION SYSTEMS AND METHODS OF USE THEREOF

(75) Inventors: David B. Masters, Minneapolis, MN (US); Eric Peter Berg, Plymouth, MN (US)

(73) Assignee: Gel-Del Technologies, Inc., St. Paul, MN (US)

( * ) Notice: Subject to any disclaimer, the term of this patent is extended or adjusted under 35 U.S.C. 154(b) by 1902 days.

(21) Appl. No.: 10/513,071

(22) PCT Filed: Apr. 29, 2003

(86) PCT No.: PCT/US03/13273
§ 371 (c)(1),
(2), (4) Date: Oct. 29, 2004

(87) PCT Pub. No.: WO03/092468
PCT Pub. Date: Nov. 13, 2003

(65) Prior Publication Data
US 2005/0163817 A1   Jul. 28, 2005

Related U.S. Application Data

(60) Provisional application No. 60/376,136, filed on Apr. 29, 2002.

(51) Int. Cl.
*A61F 13/00* (2006.01)

(52) U.S. Cl.
USPC ........................................... 424/422

(58) Field of Classification Search
None
See application file for complete search history.

(56) References Cited

U.S. PATENT DOCUMENTS

| | | | |
|---|---|---|---|
| 3,800,792 A | 4/1974 | McKnight | 602/50 |
| 3,996,934 A | 12/1976 | Zaffaroni | 424/434 |
| 4,060,081 A | 11/1977 | Yannas | 623/15.12 |
| 4,226,848 A | 10/1980 | Nagai | 514/772.1 |
| 4,250,163 A | 2/1981 | Nagai | 514/772.1 |
| 4,252,759 A | 2/1981 | Yannas | 264/86 |
| 4,280,954 A | 7/1981 | Yannas | 530/356 |
| 4,286,592 A | 9/1981 | Chandrasekaran | 424/448 |
| 4,292,299 A | 9/1981 | Suzuki | 424/435 |
| 4,347,234 A | 8/1982 | Wahlig | 424/426 |

(Continued)

FOREIGN PATENT DOCUMENTS

| | | | |
|---|---|---|---|
| CA | 1239755 | 8/1988 | A61F 2/00 |
| CA | 1245527 | 11/1988 | A61M 29/00 |
| CA | 2134997 | 11/1994 | A61F 2/04 |
| CA | 2171047 | 3/1996 | A61F 2/06 |

(Continued)

OTHER PUBLICATIONS http://www.merriam-webster.com/dictionary/binding (accessed Jan. 24, 2009).*

(Continued)

*Primary Examiner* — Paul Dickinson
(74) *Attorney, Agent, or Firm* — Patterson Thuente Pedersen, P.A.

(57) ABSTRACT

The containment and fixation system of the present invention generally includes a biomatrix sleeve, biomatrix particles or combinations thereof made of a biomatrix material. The biomatrix material is comprised of one or more biocompatible proteins and one or more biocompatible solvents. The biomatrix material utilized in the sleeve and/or particles may also include one or more pharmacologically active agents like therapeutic biochemicals such as a bone mending biochemical (e.g. hydroxyapatite) or an angiogenic growth factor (e.g. BMP).

19 Claims, 8 Drawing Sheets

(56) References Cited

U.S. PATENT DOCUMENTS

| | | | |
|---|---|---|---|
| 4,350,629 A | 9/1982 | Yannas | 530/356 |
| 4,352,883 A | 10/1982 | Lim | 435/178 |
| 4,394,370 A * | 7/1983 | Jefferies | 606/76 |
| 4,405,311 A | 9/1983 | Greatbatch | 604/20 |
| 4,418,691 A | 12/1983 | Yannas | 424/548 |
| 4,438,253 A | 3/1984 | Casey et al. | 528/86 |
| 4,448,718 A | 5/1984 | Yannas | 530/356 |
| 4,458,678 A | 7/1984 | Yannas | 602/48 |
| 4,474,752 A | 10/1984 | Haslam | 424/78 |
| 4,505,266 A | 3/1985 | Yannas | 128/898 |
| 4,517,173 A | 5/1985 | Kizawa | 424/435 |
| 4,518,721 A | 5/1985 | Dhabhar | 523/120 |
| 4,522,753 A | 6/1985 | Yannas | 530/356 |
| 4,526,938 A | 7/1985 | Churchill et al. | 525/415 |
| 4,553,545 A | 11/1985 | Maass | 606/198 |
| 4,572,832 A | 2/1986 | Kigasawa | 514/772.1 |
| 4,596,574 A | 6/1986 | Urist | 424/422 |
| 4,600,533 A | 7/1986 | Chu | 530/356 |
| 4,652,441 A | 3/1987 | Okada et al. | 424/497 |
| 4,706,680 A | 11/1987 | Keusch | 600/392 |
| 4,713,243 A | 12/1987 | Schiraldi | 424/676 |
| 4,733,665 A | 3/1988 | Palmaz | 606/108 |
| 4,734,097 A | 3/1988 | Tanabe | |
| 4,739,762 A | 4/1988 | Palmaz | 623/1.11 |
| 4,741,872 A | 5/1988 | De Luca | 264/4.7 |
| 4,780,450 A * | 10/1988 | Sauk et al. | 514/2 |
| 4,787,900 A | 11/1988 | Yannas | 600/36 |
| 4,787,906 A | 11/1988 | Haris | |
| 4,800,882 A | 1/1989 | Gianturco | 606/194 |
| 4,801,299 A | 1/1989 | Brendel | 623/1 |
| 4,849,141 A | 7/1989 | Fujioka | 264/207 |
| 4,894,232 A | 1/1990 | Reul | 424/439 |
| 4,900,554 A | 2/1990 | Yanagibashi | 424/448 |
| 4,902,289 A | 2/1990 | Yannas | 623/1.47 |
| 4,907,336 A | 3/1990 | Gianturco | 29/515 |
| 4,915,948 A | 4/1990 | Gallopo | 424/435 |
| 4,917,161 A | 4/1990 | Townend | 131/352 |
| 4,947,840 A | 8/1990 | Yannas | 602/50 |
| 4,955,893 A | 9/1990 | Yannas | 606/154 |
| 4,959,217 A | 9/1990 | Sanders | 424/473 |
| 5,004,602 A | 4/1991 | Hutchinson | |
| 5,019,372 A | 5/1991 | Folkman | 424/422 |
| 5,035,706 A | 7/1991 | Gianturco et al. | 606/198 |
| 5,037,392 A | 8/1991 | Hillstead | 606/194 |
| 5,041,126 A | 8/1991 | Gianturco | 623/1.15 |
| 5,041,292 A | 8/1991 | Feijen | 424/484 |
| 5,100,669 A | 3/1992 | Hyon et al. | 424/426 |
| 5,102,417 A | 4/1992 | Palmaz | 606/195 |
| 5,137,729 A | 8/1992 | Kuroya | 424/435 |
| 5,147,385 A | 9/1992 | Beck et al. | 128/898 |
| 5,166,187 A | 11/1992 | Collombel | 514/21 |
| 5,188,837 A | 2/1993 | Domb | 424/450 |
| 5,192,802 A | 3/1993 | Rencher | 514/535 |
| 5,211,664 A | 5/1993 | Tepic | |
| 5,260,004 A | 11/1993 | Samuelson | |
| 5,282,824 A | 2/1994 | Gianturco | 623/1.13 |
| 5,298,258 A | 3/1994 | Akemi | 424/484 |
| 5,314,915 A | 5/1994 | Rencher | 514/535 |
| 5,316,023 A | 5/1994 | Palmaz et al. | 128/898 |
| 5,324,261 A | 6/1994 | Amundson | 604/103.02 |
| 5,324,775 A | 6/1994 | Ree | 525/54.2 |
| 5,330,768 A | 7/1994 | Park et al. | 424/501 |
| 5,385,606 A | 1/1995 | Kowanko | 106/156.3 |
| 5,418,222 A | 5/1995 | Song | 514/21 |
| 5,423,739 A | 6/1995 | Phipps | 604/20 |
| 5,431,921 A | 7/1995 | Thombre | 424/424 |
| 5,443,483 A | 8/1995 | Kirsch | 606/74 |
| 5,447,940 A | 9/1995 | Harvey | 514/310 |
| 5,487,895 A | 1/1996 | Dapper | 424/278.1 |
| 5,489,304 A | 2/1996 | Orgill | 128/898 |
| 5,510,077 A | 4/1996 | Dinh | 264/485 |
| 5,512,291 A | 4/1996 | Li | 424/443 |
| 5,514,379 A | 5/1996 | Weissleder | |
| 5,518,502 A | 5/1996 | Kaplan | 600/157 |
| 5,573,934 A | 11/1996 | Hubbell | 435/177 |
| 5,607,445 A | 3/1997 | Summers | 623/1.22 |
| 5,642,749 A | 7/1997 | Perryman | 135/66 |
| 5,665,428 A | 9/1997 | Cha | 427/213.3 |
| 5,676,669 A * | 10/1997 | Colvard | 606/107 |
| 5,676,699 A * | 10/1997 | Gogolewski et al. | 623/16.11 |
| 5,709,683 A | 1/1998 | Bagby | 606/61 |
| 5,716,411 A | 2/1998 | Orgill | 435/371 |
| RE35,748 E | 3/1998 | Luck | 514/2 |
| 5,741,670 A | 4/1998 | Goetinck | 435/69.1 |
| 5,759,582 A | 6/1998 | Leong | 424/492 |
| 5,773,019 A | 6/1998 | Ashton | 424/423 |
| 5,783,214 A | 7/1998 | Royer | 424/499 |
| 5,834,232 A | 11/1998 | Bishop | 435/68.1 |
| 5,863,554 A | 1/1999 | Illum | |
| 5,879,713 A | 3/1999 | Roth | 424/489 |
| 5,948,427 A | 9/1999 | Yamamoto | 424/426 |
| 5,981,568 A | 11/1999 | Kunz | 514/411 |
| 6,004,943 A | 12/1999 | Shi | 514/44 R |
| 6,026,316 A | 2/2000 | Kucharczyk | |
| 6,048,360 A | 4/2000 | Khosravi | |
| 6,074,689 A | 6/2000 | Luck | 427/2.21 |
| 6,077,076 A | 6/2000 | Comfort | |
| 6,106,554 A | 8/2000 | Bretton | |
| 6,124,273 A | 9/2000 | Drohan | 514/55 |
| 6,179,834 B1 | 1/2001 | Buysse | 606/41 |
| 6,210,429 B1 | 4/2001 | Vardi | 623/1.11 |
| 6,248,110 B1 | 6/2001 | Reiley | 606/93 |
| 6,287,765 B1 | 9/2001 | Cubicciotti | 435/6 |
| 6,291,582 B1 | 9/2001 | Dordick | 525/54.1 |
| 6,342,250 B1 | 1/2002 | Masters | 424/484 |
| 6,371,988 B1 | 4/2002 | Pafford | 623/17.11 |
| 6,960,452 B2 | 11/2005 | Hubbell | 435/69.7 |
| 7,662,409 B2 | 2/2010 | Masters | |
| 2001/0008636 A1 | 7/2001 | Yamamoto | 424/426 |
| 2001/0020086 A1 | 9/2001 | Hubbell | 530/322 |
| 2002/0028243 A1 | 3/2002 | Masters | 424/484 |
| 2002/0052572 A1 | 5/2002 | Franco | 623/1.11 |
| 2002/0065553 A1 | 5/2002 | Weber | 606/1 |
| 2002/0141945 A1 | 10/2002 | Foster | |
| 2003/0007991 A1 | 1/2003 | Masters | 424/400 |
| 2003/0028204 A1 | 2/2003 | Li | 606/152 |
| 2003/0215515 A1 | 11/2003 | Truong-Le | |
| 2003/0225355 A1 | 12/2003 | Butler | |
| 2004/0002558 A1* | 1/2004 | McKay | 523/115 |
| 2005/0147690 A1 | 7/2005 | Masters | 424/489 |
| 2006/0073207 A1 | 4/2006 | Masters | |
| 2006/0167540 A1 | 7/2006 | Masters | |
| 2006/0210601 A1 | 9/2006 | Yunoki | |
| 2010/0143487 A1 | 6/2010 | Masters | |
| 2010/0196478 A1 | 8/2010 | Masters | |

FOREIGN PATENT DOCUMENTS

| | | | |
|---|---|---|---|
| CA | 2175722 | 5/1996 | A61F 2/04 |
| CA | 2185740 | 9/1996 | A61F 2/06 |
| CA | 2192520 | 12/1996 | A61F 2/06 |
| EP | 0082621 | 6/1983 | |
| EP | 0099758 | 2/1984 | |
| EP | 0258780 A2 | 8/1987 | |
| EP | 0 567 234 A1 | 3/1993 | A61K 47/42 |
| EP | 0 636 378 B1 | 7/1994 | A61L 31/00 |
| FR | 2247258 | 5/1975 | |
| WO | WO 93/24150 | 12/1993 | A61K 47/48 |
| WO | WO9422423 | 10/1994 | |
| WO | WO 97/32543 | 9/1997 | A61F 2/06 |
| WO | WO 97/32544 | 9/1997 | A61F 2/06 |
| WO | WO 97/41803 | 11/1997 | A61F 2/06 |
| WO | WO 99/32613 A1 | 7/1999 | C12N 9/98 |
| WO | WO9932107 | 7/1999 | |
| WO | WO9937240 | 7/1999 | |
| WO | WO0128524 | 4/2001 | |
| WO | WO 0183522 A2 | 11/2001 | C07K 14/00 |
| WO | WO 0187267 A1 | 11/2001 | A61K 9/10 |
| WO | WO02058735 | 8/2002 | |

OTHER PUBLICATIONS

AAPS: Annual Meeting & Exposition, *Symposia Abstracts & Biographies*, Boston, MA, Nov. 2, 1997, pp. 25-27.

(56) References Cited

OTHER PUBLICATIONS

Abbott, et al., *Vascular Grafts: Characteristics and Routine Selection of Prostheses*, Vascular Surgery, a Comprehensive Review, 5th Edition.
Abstracts, *Eighth International Symposium on Recent Advances in Drug Delivery Systems*, Feb. 24, 1997, Salt Lake City, UT, pp. 36-39, 138-140.
*American Red Cross Open to Partners for New Fibrin Sealant*, Genetic Engineering News, Mar. 1995, p. 30.
Anderson, *Characterization of Silk-like Proteins and Processing for Biomedical Applications*, Protein-Based Materials, 1997, pp. 371-423.
*The Biological Production of Protein Polymers and Their Use*, Trends in Biotechnology, Nov. 1990, vol. 8, No. 11.
Cappello, et al., *Microbial Production of Structural Polymers*, (ed. Mobley), 1994 Carl Hanser Verlag, Munich, pp. 35-92.
Cappello, et al., *Genetic Engineering of Structural Protein Polymers*, Biotechnology Progress, 1990, pp. 198-202.
Cappello, *Protein Engineering for Biomaterials Applications*, Current Opinion in Structural Biology, 1992, 2:582-586.
Caruana, *New Drugs Spur Novel Delivery Systems*, Chemical Engineering Progress, Jul. 1997, pp. 15-19.
Choi, et al. Implantation Biology: The Host Response and Biomedical Devices. *The Effect of Biomaterials on the Host*, CRC Press, Boca Raton 405 pages, 1994. Chapter 3, pp. 39-53.
Chvapil, et al., *Some Chemical and Biological Characteristics of a New Collagen-Polymer\* Compound Material*, J. Biomed. Mater. Res. vol. 3, pp. 315-331 (1969).
Davis, et al., *Chemically Cross-Linked Albumin Microspheres for the Controlled Release of Incorporated Rose Bengal After Instramuscular Injection Into Rabbits*, Journal of Controlled Release, 4 (1987) 293-302.
Dickinson, et al., *Biodegradation of a poly($\alpha$-amino acid) hydrogel. I. In vivo*, Journal of Biomedical Materials Research, vol. 15, 577-589 (1981).
Drug Delivery Systems (Program), Feb. 1998, San Francisco.
Dunn, et al., *Biomaterials Used in Orthopaedic Surgery*, Implantation Biology, CRC Press, Boca Raton, 1994, pp. 229-252.
Dutton, *Tissue Engineering: Continued Growth Expected as New Techniques Evolve*, Genetic Engineering News, Apr. 1998, pp. 21, 37.
Fernandes, et al., *Regulation of Polymeric Implants for Site-specific Drug Delivery*, Polymeric Site-specific Pharmcotherapy, Chapter 16, pp. 424-441.
Ghandehari, et al., *Genetic Engineering of Protein-Based Polymers: Potential in Controlled Drug Delivery*, Pharmaceutical Research, vol. 15, No. 6, 1998, pp. 813-815.
Harvey, *Utilizing Prostheses for Drug Delivery*, Implantation Biology, CRC Press, Boca Raton, 1994, pp. 329-345.
Heller, et al., *Controlled release of water-soluble macromolecules from Bioerodible Hydrogels*, Biomaterials 1983, vol. 4 October, pp. 262-266.
Kelly, *Researchers Advancing Biopolymer Systems as Vehicles for Delivering Drugs*, Genetic Engineering News, May 15, 1997, pp. 1, 25, 32, 35, 36, 41.
Langer, *1994 Whitaker Lecture: Polymers for Drug Delivery and Tissue Engineering*, Annals of Biomedical Engineering, 1995, vol. 23, pp. 101-111.
Lewis, *New Directions in Research on Blood Substitutes*, Genetic Engineering News, Jun. 15, 1997, pp. 1, 10, 12, 20, 26, 33, 35, 36, 41.
Li, et al, *A Novel Biodegradable System Based on Gelatin Nanoparticles and Poly(lactic-co-glycolic acid) Microspheres for Protein and Peptide Drug Delivery*, Journal of Pharmaceutical Sciences, vol. 86, No. 8, Aug. 1997, p. 891-895.
Masters, et al., *Liposphere Local Anesthetic Timed-Release for Perineural Site Application*, Pharmaceutical Research, vol. 15, No. 7, 1998, pp. 1038-1045.
Masters, et al., *Sustained Local Anesthetic Relapse from Bioerodible Polymer Matrices: A Potential Method for Prolonged Regional Anesthesia*, Pharmaceutical Research, vol. 10, No. 10, 1993, pp. 1527-1532.
Masters, Course Syllabus for Mayo Graduate Course, *Polymeric Site-Specific Drug Delivery*, Apr. 1998.
Masters, et al., *Prolonged Regional Nerve Blockade by Controlled Release of Local Anesthetic from a Biodegradable Polymer Matrix*, Anesthesiology, vol. 79, No. 2, 1993, pp. 340-346.
Masters, *Drug Delivery to Peripheral Nerves*, Polymeric Site-Specific Pharmacotherapy, 1994, pp. 443-455.
Morrow, *Companies to Take Broad Range of Approaches to Develop Rheumatoid Arthritis Therapies*, Genetic Engineering News, Jan. 15, 1997, pp. 1, 7, 9, 24.
Ohtani, *Three-Dimensional Organization of the Collagen Fibrillar Framework of the Human and Rat Livers*, Arch. Hist. Cytol., vol. 51, No. 5, 1988, pp. 473-788.
Peppas, et al. *New Challenges in Biomaterials*, Science, Mar. 1994, vol. 263, pp. 1715-1720.
Pramik, *Drug Delivery Firms Focus on Controlled Release Techniques*, Genetic Engineering News, Oct. 1, 1996, pp. 1, 38, 40.
Pramik, *Positive Clinical Results in Pulmonary Drug Delivery: Inhaled Insulin Effective as Injected Drug*, Genetic Engineering News, Jul. 1998, vol. 18, No. 13, pp. 1, 12, 35, 46.
Protein Polymer Technologies: 1994 Annual Report, *BioEngineered Tissue Repair and Regeneration*.
R&D, A Cahners Publication, *BioDerived Materials*, Jun. 1990, p. 58.
Ranade, *Drug Delivery Systems: 3A. Role of Polymers in Drug Delivery*, J.Clin. Pharmacol 1990; 30: 10-23.
Ranade, *Drug Delivery Systems: 3A. Role of Polymers in Drug Delivery*, J.Clin. Pharmacol 1990; 30: 107-120.
Ratner, et al., *An Introduction to Materials in Medicine*, Biomaterials Science, 1996.
Sedlak, *Hyal Pharmaceutical Looks for Home Run with HIT Drug Delivery System*, Genetic Engineering News, Sep. 1, 1995, p. 16.
Sedlak, *Signal Transduction Companies Moving Some Products to the Clinical Testing Environment*, Genetic Engineering News, Mar. 15, 1997, vol. 17, No. 6, pp. 1, 27, 36.
Skarda, et al., *Biodegradable Hydrogel for Controlled Release of Biologically Active Macromolecules*, Journal of Bioactive and Compatible Polymers, vol. 8, Jan. 1993, pp. 24-40.
*Tissue Engineering*, Genetic Engineering News, Jan. 1998, pp. 33.
Urry, et al., *Protein-Based Materials with a Profound Range of Properties and Applications: The Elastin $\Delta T_t$ Hydrophobic Paradigm*, Protein-Based Materials, 1997, pp. 133-177.

\* cited by examiner

BIOMATRIX STRUCTURAL CONTAINMENT AND FIXATION SYSTEMS AND METHODS OF USE THEREOF

PRIORITY CLAIM

The present application is a National Phase entry of PCT Application No. PCT/US03/13273, filed Apr. 29, 2003, which claims the benefit of U.S. Provisional Application No. 60/376,136, filed Apr. 29, 2002, the disclosures of which are hereby incorporated by reference herein in their entirety.

BACKGROUND OF THE INVENTION

Fractures are a common clinical condition. In 1997 in the United States alone, there were approximately eight million fractures. In the same time period there were more than 25 million worldwide. In the treatment of fractures more than 740,000 repair procedures were performed at US hospitals. Of the fracture repair procedures, a total of 9,110 open-reduction without internal fixation procedures were performed and a total of 468,310 open-reduction with internal fixation procedures were performed. Some key statistics that are applicable to the specific scope of the current study are those related to non-unions and malunions. It has been reported that between 2-7% of fractures are nonunions. Many of the non-union fractures occur in the tibia. The overall rate of delayed union in tibia fractures ranges from 5-61%, and the rate for nonunions in tibial fractures vary from 0-21%.

The number of procedures that could utilize the proposed fracture fixation sleeve of the present invention includes the open-reduction procedures primarily of long bone fractures (477,420 procedures). In particular, the procedures that utilize bone graft or orthobiologic agents (10%) would be applicable (47,720 procedures). Also of note would be the non-union fractures (14,800 procedures).

One major goal of orthopaedic surgery is to incorporate methods that will stimulate the healing of bone. Many methods of treatment yield successful results, however complications do arise. Bone grafts and synthetic materials are often applied in these circumstances. Basic science has progressed this area of orthopaedics a great deal, however a continued need for quality research and new, useful products exists. The dynamic nature of bone and its ability to repair itself makes this a challenging endeavor in the orthopaedic community.

Bone is a material that is characterized by cells and mineral salts embedded in a fibrous matrix. Each of the base materials of bone supply essential components of the strength which are required to maintain the overall mechanical function of osseous tissue. Among two of the key elemental materials leading to the functional strength of bone are Type I collagen and hydroxyapatite (HAp). The fibrous matrix of bone is comprised primarily of collagen (90%). Type I collagen is required for the tensile strength in bone. Bones are required to maintain a significant amount of tensile strength resistance due to the bending loads that are applied during normal functioning. The strength and rigid nature of bone is due to the mineral component of the material. In bone, the mineral component consists mainly of hydroxyapatite. The combination of the basic substrates of bone leads to a material that can resist and transfer both tensile and compressive loads.

A fracture occurs when the forces that are applied exceed the load bearing capacity of the bone. The result is structural failure. The load applied, the direction of the load, the size and geometry of the bone, and the material properties of the bone are all factors in determining if or when a bone will fracture. Several mechanisms play a role in the healing of a bone after fracture. There are biochemical, biomechanical, cellular, hormonal, and pathological factors that influence the bone healing process.

The healing process of bone resembles the early stages of bone development. The injured area first goes through an inflammatory stage characterized by the migration of cells to the region and followed by an ingrowth of vascular tissue into the affected area. The next phase of fracture healing involves the development of a supportive connective tissue generated by fibroblasts. The connective tissue network supports the vascular growth into the area as healing takes place. Finally, the fracture healing process is completed with the remodeling phase. The goal of the remodeling phase is to return the bone to its original shape, structure, and mechanical strength. The remodeling process is time dependent. It is characterized by a process whereby the bone reacts to the mechanical stress it is subjected to through a dynamic resorption/growth process. As a bone is mechanically loaded, it will respond by building new tissue, realigning the matrix and minerals, and resorption of bone where adequate loading is not present. There are several reasons why fractures fail to heal. Among these are: inadequate immobilization, comminuted and devascularized bone, poor vascularity, infection, prior irradiation, bony defects, systemic factors, reaction to medications, and smoking. The failure of a fracture to heal is considered a non-union or delayed union fracture.

Non-union or delayed-union fractures are among the most difficult to treat. Fractures that do not properly heal resulting in a delayed or nonunion may require several surgeries utilizing a variety of techniques. Surgical methods utilized in the treatment of such fractures include: plating, internal fixation, intramedullary nails, and the use of bone grafting or bone substitute materials. Failure of the surgical methods can result in pseudoarthritis of the fracture site, instability, loss of weight-bearing ability, and painful, device assisted ambulation.

One method that is utilized extensively in the treatment of the specified fractures is the use of bone grafting or the use of bone substitutes. Materials that are used can be either osteogenic, osteoconductive, or osteoinductive. A variety of materials are used, but they can be divided into several specific groups. The generalized categories are autograft, allograft, xenograft, synthetic materials, and various combinations.

Despite many advances in the methods to treat these specified fractures using implanted medical devices including synthetic materials, there are still concerns with the ability of synthetic materials to integrate with the body's tissues. The use of materials produced from the body's own biopolymers can reduce the risk of detrimental effects and increase the body's ability to regenerate itself. Natural biomaterials have been researched, however they have not been shown to demonstrate the required physical properties required for implant systems.

SUMMARY OF THE INVENTION

The treatment of segmental defects, nonunion, and delayed union bone fractures remains a severe clinical problem. As one study concluded "Management of severe lower extremity fractures . . . could be improved by methods that stimulate and accelerate the fracture healing process." The present invention is aimed at filling this essential clinical need. The innovation of this concept is directed both in the production of a new, biocompatible matrix material and a new application within the field of orthopedic surgery to treat these selected bone fractures. More specifically, the present invention comprises a protein biomatrix containment sleeve, biomatrix particle forms and combinations thereof. In various embodiments of the present invention, the containment sleeve and/or particles include a bone mending biochemical, such as hydroxyapatite into the biomatrix material comprised of proteins such as collagen and elastin and one or more biocompatible solvents such as water. Additionally, the present invention further includes a method for implanting and securing an implant system comprised of the biomatrix containment sleeve and particles.

The long-term goal of the fracture fixation system is to enable bone to heal across defects through osteoconductive regeneration directed and contained by a biomatrix sleeve and induced by biomatrix particles administered into the defect. This technology offers a new and simplified treatment method for fractures that are exceptionally difficult to treat and a basis to develop these products.

Furthermore, embodiments of the present invention improve local anesthetic blockade of peripheral nerves by using a biocompatible protein matrix drug delivery system. Other embodiments of the present invention also stimulate peripheral nerve response due to the implanted local anesthetic thereby reducing acute pain. The effects of prolonged local anesthetic block have been determined, in vivo. It was found that protein biomatrices of the present invention can be utilized to deliver local anesthetic agents to create nerve block for days to weeks and that the underlying pain mediating biochemicals could be altered by this treatment, suggesting that prolonged nerve block can alter chronic pain mechanisms.

An embodiment of the present invention comprises a protein biomatrix in both sheet or sleeve and particle form that incorporates both hydroxyapatite (HAp) and collagen for use in the treatment of orthopedic injuries. However, it is noted that other biocompatible proteins and reagents may also be utilized in the present invention.

Another embodiment of the present invention includes a method of implanting and securing an implant system combining both biomatrix sheet and particle form for the treatment of segmental defects, nonunion, and delayed union fractures.

Still another embodiment of the present invention includes a method of making an implant system including a biomaterial in both sheet or sleeve and particle form for the treatment of segmental defects, nonunion and delayed union fractures.

The current invention is intended to provide new materials, devices and treatment methods to address non union fractures or those characterized by segmented defects or other bone fractures that heal slowly or not well due to disease, trauma or age. However, the present invention may also be utilized to repair fractures or damage to other parts of the body such as tendons and nerves (e.g. spinal cord and optical nerve). The present invention improves current therapies by using both a containment sleeve to isolate bone, tendon or nerve healing from soft tissue and by adding therapeutic bone, tendon or nerve mending particles, such as collagen-HAp particles to act as healing scaffolds, both of which provide local drug delivery and local cell integration to the site of healing. For example the administration of sleeves and/or particles including bone mending biochemicals (e.g., hydroxyapatite), growth factors (e.g., bone morphogenic protein) or other therapeutic agents (e.g., antibacterial, analgesics, anesthetic) can assist in reducing the time of recovery and enhance the proper mending of the injured part of the body. Finally, the containment and fixation device can facilitate and organize wound healing with and without the addition of growth factors (e.g. angiogenic growth factors) and/or other drugs. For example, the sleeve and particles of the present invention provides organization for the surrounding bone and tissue to heal along a defined scaffolding rather than healing over a tissue and/or bone defect. The containment sleeve being in close contact with the periosteal bone/tissue further promotes the vascularization during healing by providing a connection across the defect.

DETAILED DESCRIPTION OF THE INVENTION

Figure 1:
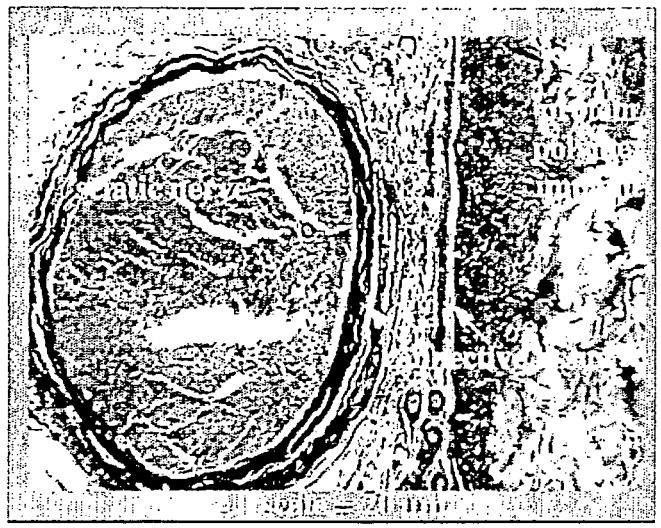
FIG. 1 depicts a histology slide from a sciatic nerve study including one embodiment of the biomatrix material of the present invention.

The fixation system of the present invention generally includes a containment and fixation sleeve, biomatrix particles or combinations thereof. In many embodiments of the present invention, the sleeve and particles are commonly made of a biomatrix material. The biomatrix material is comprised of one or more biocompatible proteins and one or more biocompatible solvents. The biomatrix material utilized in the sleeve and/or particles may also include one or more therapeutic biochemicals such as a bone mending biochemical, such as hydroxyapatite or an angiogenic growth factor such as BMP.

The biomatrix material is designed to retain the protein's natural activity combined with the ability to form it into various shapes with structural integrity. The biomatrix material is further designed to mimic the architectural framework of the body to support natural tissue growth. The biomatrix material is biointegratable thereby allowing the integration and remodeling of the biomatrix material by the host tissue. In addition to the ability to act as a structural scaffold, the ability to customize the material properties to the application, to mold the material into any defined shape, and to incorporate other substances such as pharmacologically active agents (drugs), particles, or other structural materials, into the base matrix also make the biomatrix material unique.

As previously mentioned the biomatrix materials are generally comprised of one or more biocompatible proteins, one or more biocompatible solvents and optionally one or more pharmacologically active agents. It is noted that additional additive materials such as polymers and/or therapeutic entities may be included in the material to provide various beneficial features such as strength, elasticity, structure, enhanced biocompatibility and/or any other desirable characteristics. In various embodiments of the present invention, the sleeves and/or particles prepared utilizing the biomatrix materials possess a relatively homogeneous distribution of the components, including a homogenous distribution of any bone mending biochemicals, angiogenic growth factors or other pharmacologically active agents.

The biomatrix materials normally comprise one or more biocompatible synthetic proteins, genetically-engineered proteins, natural proteins or any combination thereof. In many embodiments of the present invention, the biomatrix materials comprise a water-absorbing, biocompatible protein. The utilization of a water-absorbing biocompatible protein provides the advantage that, not only will the biocompatible protein particles be bioresorbable, but may remodel to mimic and support the tissue it contacts. That is, the metabolites of any degradation and/or resorption of the water-absorbing biocompatible protein may be reused by the patient's body rather than excreted.

Additionally, the proteins of the present invention are generally purified and in a free-form state. Normally, free-form proteins are comprised of protein molecules that are not substantially crosslinked to other protein molecules, unlike tissues or gelatins. Normally, tissue or gelatin is already in a crosslinked matrix form and is thereby limited in forming new intermolecular or intramolecular bonds. Therefore, the free-form protein molecules when added to solvent have the capacity to freely associate or intermingle with each other and other molecules or particles, such as solvents or pharmacologically active agents.

As previously suggested, the biocompatible protein utilized may either be naturally occurring, synthetic or genetically engineered. Naturally occurring protein that may be utilized in the containment and fixation system of the present invention include, but are not limited to elastin, collagen, albumin, ovalbumin, keratin, fibronectin, silk, silk fibroin, actin, myosin, fibrinogen, thrombin, aprotinin, antithrombin III and any other biocompatible natural protein. Examples of proteins that are commercially available and may be utilized in some embodiments of the present invention include Type I soluble or insoluable collagen, insoluable or soluable elastin, soluable albumen manufactured by Kensey Nash Corporation, 55 East Uwchlan Avenue, Exton, Pa. 19341, Sigma-Aldrich Corporation, St. Louis, Mo., USA or Elastin Products Company, Inc., P.O. Box 568, Owensville, Mo., USA 65066. It is noted that combinations of natural proteins may be utilized to optimize desirable characteristics of the resulting biomatrix materials, such as strength, degradability, resorption, etc. Inasmuch as heterogeneity in molecular weight, sequence and stereochemistry can influence the function of a protein in a biomatrix material, in some embodiments of the present invention synthetic or genetically engineered proteins are preferred in that a higher degree of control can be exercised over these parameters.

As previously suggested the proteins of the present invention are generally purified proteins. The purity of each natural protein component mixed in the coatable composition phase (the coatable composition will be described further below) during production of particles include 20% or less other proteins or impurities, preferably 10% or less other proteins or impurities, more preferably 3% or less other proteins or impurities and if available ideally 1% or less other proteins or impuritites.

Synthetic proteins are generally prepared by chemical synthesis utilizing techniques known in the art. Also, individual proteins may be chemically combined with one or more other proteins of the same or different type to produce a dimer, trimer or other multimer. A simple advantage of having a larger protein molecule is that it will make interconnections with other protein molecules to create a stronger biomatrix material that is less susceptible to dissolving in aqueous solutions and provides additional protein structural and biochemical characteristics.

Additional, protein molecules can also be chemically combined to any other chemical so that the chemical does not release from the biomatrix materials. In this way, the chemical entity can provide surface modifications to the biomatrix materials or structural contributions to the material to produce specific characteristics. The surface modifications can enhance and/or facilitate cell attachment depending on the chemical substance or the cell type. The structural modifications can be used to facilitate or impede dissolution, enzymatic degradation or dissolution of the biomatrix material.

Synthetic biocompatible proteins may be cross-linked, linked, bonded, chemically and/or physically linked to pharmacological active agents, enzymatically, chemically or thermally cleaved and utilized alone or in combination with other biocompatible proteins or partial proteins e.g. peptides, to form the biomatrix materials. Examples of such synthetic biocompatible proteins include, but are not limited to heparin-protein, heparin-polymer, chondroitin-protein, chondroitin-polymer, heparin-cellulose, heparin-alginate, heparin-polylactide, GAGs-collagen, heparin-collagen, collagen-elastin-heparin, collagen-albumin, collagen-albumin-elastin-heparin, collagen-hyaluronic acid, collagen-albumin-heparin, collagen-chondroitin-heparin, collagen-chondroitin and the like.

A specific example of a particularly preferred genetically engineered protein for use in the biocompatible protein particles of the present invention is human collagen produced by FibroGen, Inc., 225 Gateway Blvd., South San Francisco, Calif. 94080. Other specific examples of particularly preferred genetically engineered proteins for use in the biomatrix materials of the present invention are commercially available under the nomenclature "ELP", "SLP", "CLP", "SLPL", "SLPF" and "SELP" from Protein Polymer Technologies, Inc. San Diego, Calif. ELP's, SLP's, CLP's, SLPL's, SLPF's and SELP's are families of genetically engineered protein polymers consisting of silklike blocks, elastinlike blocks, collagenlike blocks, lamininlike blocks, fibronectinlike blocks and the combination of silklike and elastinlike blocks, respectively. The ELP's, SLP's, CLP's, SLPL's, SLPF's and SELP's are produced in various block lengths and compositional ratios. Generally, blocks include groups of repeating amino acids malting up a peptide sequence that occurs in a protein. Genetically engineered proteins are qualitatively distinguished from sequential polypeptides found in nature in that the length of their block repeats can be greater (up to several hundred amino acids versus less than ten for sequential polypeptides) and the sequence of their block repeats can be almost infinitely complex. Table A depicts examples of genetically engineered blocks. Table A and a further description of genetically engineered blocks may be found in Franco A. Ferrari and Joseph Cappello, *Biosynthesis of Protein Polymers*, in: Protein-Based Materials, (eds., Kevin McGrath and David Kaplan), Chapter 2, pp. 37-60, Birkhauser, Boston (1997).

TABLE A

Protein polymer sequences

| Polymer Name | Monomer Amino Acid Sequence |
|---|---|
| SLP 3 | [(GAGAGS)$_9$GAAGY)] |
| SLP4 | (GAGAGS)$_n$ |
| SLP F | [(GAGAGS)$_9$GAA VTGRGDSPAS AAGY]$_n$ |

TABLE A-continued

Protein polymer sequences

| Polymer Name | Monomer Amino Acid Sequence |
|---|---|
| SLP L3.0 | [(GAGAGS)$_9$GAA PGASIKVAVSAGPS AGY]$_n$ |
| SLP L3.1 | [(GAGAGS)$_9$GAA PGASIKVAVSGPS AGY]$_n$ |
| SLP F9 | [(GAGAGS)$_9$RYVVLPRPVCFEK AAGY]$_n$ |
| ELP I | [(VPGVG)$_4$]$_n$ |
| SELP 0 | [(GVGVP)$_8$(GAGAGS)$_2$]$_n$ |
| SELP 1 | [GAA (VPGVG)$_4$ VAAGY (GAGAGS)$_9$]$_n$ |
| SELP 2 | [(GAGAGS)$_6$GAAGY (GAGAGS)$_5$(GVGVP)$_8$]$_n$ |
| SELP 3 | [(GVGVP)$_8$(GAGAGS)$_8$]$_n$ |
| SELP 4 | [(GVGVP)$_{12}$(GAGAGS)$_8$]$_n$ |
| SELP 5 | [(GVGVP)$_{16}$(GAGAGS)$_8$]$_n$ |
| SELP 6 | [(GVGVP)$_{32}$(GAGAGS)$_8$]$_n$ |
| SELP 7 | [(GVGVP)$_8$(GAGAGS)$_6$]$_n$ |
| SELP 8 | [(GVGVP)$_8$(GAGAGS)$_4$]$_n$ |
| KLP 1.2 | [(AKLKLAEAKLELAE)$_4$]$_n$ |
| CLP 1 | [GAP(GPP)$_4$]$_n$ |
| CLP 2 | {[GAP(GPP)$_4$]$_2$ GPAGPVGSP}$_n$ |
| CLP-CB | {[GAP(GPP)$_4$]$_2$ (GLPGPKGDRGDAGPKGADGSPGPA) GPAGPVGSP}$_n$ |
| CLP 3 | (GAPGAPGSQGAPGLQ)$_n$ |

Repetitive amino acid sequences of selected protein polymers.
SLP = silk like protein;
SLPF = SLP containing the RGD sequence from fibronectin;
SLPL 3/0 and SLPL 3/1 = SLP containing two difference sequences from laminin protein;
ELP = elastin like protein;
SELP = silk elastin like protein;
CLP = collagen like protein;
CLP-CB = CLP containing a cell binding domain from human collagen;
KLP = keratin like protein The nature of the elastinlike blocks, and their length and position within the monomers influences the water solubility of the SELP polymers. For example, decreasing the length and/or content of the silklike block domains, while maintaining the length of the elastinlike block domains, increases the water solubility of the polymers. For a more detailed discussion of the production of SLP's, ELP's, CLP's, SLPF's and SELP's as well as their properties and characteristics see, for example, in J. Cappello et al., *Biotechnol. Prog.*, 6, 198 (1990), the full disclosure of which is incorporated by reference herein. One preferred SELP, SELP7, has an elastin:silk ratio of 1.33, and has 45% silklike protein material and is believed to have weight average molecular weight of 80,338.

The biomatrix material utilized in various embodiments of the present invention also include one or more biocompatible solvents. Any biocompatible solvent may be utilized in the method and corresponding biomatrix material of the present invention. By using a biocompatible solvent, the risk of adverse tissue reactions to residual solvent remaining in the device after manufacture is minimized. Additionally, the use of a biocompatible solvent reduces the potential structural and/or pharmacological degradation of the pharmacologically active agent that some such pharmacologically active agents undergo when exposed to organic solvents. Suitable biocompatible solvents for use in the method of the present invention include, but are not limited to, water; dimethyl sulfoxide (DMSO); biocompatible alcohols, such as glycerol, methanol and ethanol; various acids, such as formic acid; oils, such as olive oil, peanut oil and the like; ethylene glycol, glycols; and combinations of these and the like. Preferably, the biocompatible solvent comprises water. The amount of biocompatible solvent utilized in the coatable composition will preferably be that amount sufficient to result in the composition being fluid and flowable enough to be coatable. Generally, the amount of biocompatible solvent suitable for use in the method of the present invention will range from about 50% to about 1000%, preferably from about 100% to about 300% by weight, based upon the weight and/or amount of the protein utilized.

In addition to the biocompatible protein(s) and the biocompatible solvent(s), the biomatrix material that may be utilized in various embodiments of the present invention may include one or more pharmacologically active agents. As used herein, "pharmacologically active agent" generally refers to a pharmacologically active agent having a direct or indirect beneficial therapeutic effect upon introduction into a host. Pharmacologically active agents further includes neutraceuticals. The phrase "pharmacologically active agent" is also meant to indicate prodrug forms thereof. A "prodrug form" of a pharmacologically active agent means a structurally related compound or derivative of the pharmacologically active agent which, when administered to a host is converted into the desired pharmacologically active agent. A prodrug form may have little or none of the desired pharmacological activity exhibited by the pharmacologically active agent to which it is converted. Representative examples of pharmacologically active agents that may be suitable for use in the protein matrix device of the present invention include, but are not limited to, (grouped by therapeutic class):

Antidiarrhoeals such as diphenoxylate, loperamide and hyoscyamine;

Antihypertensives such as hydralazine, minoxidil, captopril, enalapril, clonidine, prazosin, debrisoquine, diazoxide, guanethidine, methyldopa, reserpine, trimethaphan;

Calcium channel blockers such as diltiazem, felodipine, amlodipine, nitrendipine, nifedipine and verapamil;

Antiarrhyrthmics such as amiodarone, flecainide, disopyramide, procainamide, mexiletene and quinidine, Antiangina agents such as glyceryl trinitrate, erythrityl tetranitrate, pentaerythritol tetranitrate, mannitol hexanitrate, perhexilene, isosorbide dinitrate and nicorandil;

Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate;

Cardiotonic glycosides such as digoxin and other cardiac glycosides and theophylline derivatives;

Adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine;

Vasodilators such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol;

Antiproliferative agents such as paclitaxel, actinomycin D, sirolimus, tacrolimus, everolimus and dexamethasone;

Antimigraine preparations such as ergotanmine, dihydroergotamine, methysergide, pizotifen and sumatriptan;

Anticoagulants and thrombolytic agents such as warfarin, dicoumarol, low molecular weight heparins such as enoxaparin, streptokinase and its active derivatives;

Hemostatic agents such as aprotinin, tranexamic acid and protamine;

Analgesics and antipyretics including the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenopefidine, codeine dihydrocodeine; acetylsalicylic acid (aspirin), paracetamol, and phenazone;

Immunosuppressants, antiproliferatives and cytostatic agents such as rapomycin (sirolimus) and its analogs (everolimus and tacrolimus);

Neurotoxins such as capsaicin, botulinum toxin (botox);

Hypnotics and sedatives such as the barbiturates amylobarbitone, butobarbitone and pentobarbitone and other hypnotics and sedatives such as chloral hydrate, chlomethiazole, hydroxyzine and meprobamate;

Antianxiety agents such as the benzodiazepines alprazolam, bromazepam, chlordiazepoxide, clobazam, chlorazepate, diazepam, flunitrazepam, flurazepam, lorazepam, nitrazepam, oxazepam, temazepam and triazolam;

Neuroleptic and antipsychotic drugs such as the phenothiazines, chlorpromazine, fluphenazine, pericyazine, perphenazine, promazine, thiopropazate, thioridazine, trifluoperazine; and butyrophenone, droperidol and haloperidol; and other antipsychotic drugs such as pimozide, thiothixene and lithium;

Antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline;

CNS stimulants such as caffeine and 3-(2-aminobutyl)indole;

Anti-alzheimer's agents such as tacrine;

Anti-Parkinson's agents such as amantadine, benserazide, carbidopa, levodopa, benztropine, biperiden, benzhexol, procyclidine and dopamine-2 agonists such as S(−)-2-(N-propyl-N-2-thienylethylamino)-5-hydroxytetralin (N-0923), Anticonvulsants such as phenytoin, valproic acid, primidone, phenobarbitone, methylphenobarbitone and carbamazepine, ethosuximide, methsuximide, phensuximide, sulthiame and clonazepam, Antiemetics and antinauseants such as the phenothiazines prochloperazine, thiethylperazine and 5HT-3 receptor antagonists such as ondansetron and granisetron, as well as dimenhydrinate, diphenhydramine, metoclopramide, domperidone, hyoscine, hyoscine hydrobromide, hyoscine hydrochloride, clebopride and brompride;

Non-steroidal anti-inflammatory agents including their racemic mixtures or individual enantiomers where applicable, preferably which can be formulated in combination with dermal and/or mucosal penetration enhancers, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketorolac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate;

Antirheumatoid agents such as penicillamine, aurothioglucose, sodium aurothiomalate, methotrexate and auranofin;

Muscle relaxants such as baclofen, diazepam, cyclobenzaprine hydrochloride, dantrolene, methocarbamol, orphenadrine and quinine;

Agents used in gout and hyperuricaemia such as allopurinol, colchicine, probenecid and sulphinpyrazone;

Oestrogens such as oestradiol, oestriol, oestrone, ethinyloestradiol, mestranol, stilboestrol, dienoestrol, epioestriol, estropipate and zeranol;

Progesterone and other progestagens such as allyloestrenol, dydrgesterone, lynoestrenol, norgestrel, norethyndrel, norethisterone, norethisterone acetate, gestodene, levonorgestrel, medroxyprogesterone and megestrol;

Antiandrogens such as cyproterone acetate and danazol;

Antioestrogens such as tamoxifen and epitiostanol and the aromatase inhibitors, exemestane and 4-hydroxy-androstenedione and its derivatives;

Androgens and anabolic agents such as testosterone, methyltestosterone, clostebol acetate, drostanolone, furazabol, nandrolone oxandrolone, stanozolol, trenbolone acetate, dihydro-testosterone, 17-(α-methyl-19-noriestosterone and fluoxymesterone;

5-alpha reductase inhibitors such as finasteride, turosteride, LY-191704 and MK-306;

Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate, methylprednisolone, prednisolone, prednisolone 21-phosphate, prednisone, triamcinolone, triamcinolone acetonide;

Glycosylated proteins, proteoglycans, glycosaminoglycans such as chondroitin sulfate; chitin, acetyl-glucosamine, hyaluronic acid;

Complex carbohydrates such as glucans;

Further examples of steroidal anti-inflammatory agents such as cortodoxone, fludroracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlolisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, aincinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol;

Pituitary hormones and their active derivatives or analogs such as corticotrophin, thyrotropin, follicle stimulating hormone (FSH), luteinising hormone (LH) and gonadotrophin releasing hormone (GnRH);

Hypoglycemic agents such as insulin, chlorpropamide, glibenclamide, gliclazide, glipizide, tolazamide, tolbutamide and metformin;

Thyroid hormones such as calcitonin, thyroxine and liothyronine and antithyroid agents such as carbimazole and propylthiouracil;

Other miscellaneous hormone agents such as octreotide;

Pituitary inhibitors such as bromocriptine;

Ovulation inducers such as clomiphene;

Diuretics such as the thiazides, related diuretics and loop diuretics, bendrofluazide, chliorothiazide, chlorthalidone, dopamine, cyclopenthiazide, hydrochlorothiazide, indapamide, mefruside, methycholthiazide, metolazone, quinethazone, bumetanide, ethacrynic acid and frusemide and potasium sparing diuretics, spironolactone, amiloride and triamterene;

Antidiuretics such as desmopressin, lypressin and vasopressin including their active derivatives or analogs;

Obstetric drugs including agents acting on the uterus such as ergometrine, oxytocin and gemeprost;

Prostaglandins such as alprostadil (PGE1), prostacyclin (PGI2), dinoprost (prostaglandin F2-alpha) and misoprostol;

Antimicrobials including the cephalosporins such as cephalexin, cefoxytin and cephalothin;

Penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, meziocillin, piperacillin, ticarcillin and azlocillin;

Tetracyclines such as minocycline, chlortetracycline, tetracycline, demeclocycline, doxycycline, methacycline and oxytetracycline and other tetracycline-type antibiotics;

Amnioglycoides such as amikacin, gentamicin, kanamycin, neomycin, netilmicin and tobramycin;

Antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione;

Quinolones such as nalidixic acid, cinoxacin, ciprofloxacin, enoxacin and norfloxacin;

Sulphonamides such as phthalysulphthiazole, sulfadoxine, sulphadiazine, sulphamethizole and sulphamethoxazole;

Sulphones such as dapsone;

Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonarn, colistin IV, metronidazole, tinidazole, fusidic acid, trimethoprim, and 2-thiopyridine N-oxide; halogen compounds, particularly iodine and iodine compounds such as iodine-PVP complex and diiodohydroxyquin, hexachlorophene; chlorhexidine; chloroamine compounds; and benzoylperoxide;

Antituberculosis drugs such as ethambutol, isoniazid, pyrazinamide, rifampicin and clofazimine;

Antimalarials such as primaquine, pyrimethamine, chloroquine, hydroxychloroquine, quinine, mefloquine and halofantrine;

Antiviral agents such as acyclovir and acyclovir prodrugs, famcyclovir, zidovudine, didanosine, stavudine, lamivudine, zalcitabine, saquinavir, indinavir, ritonavir, n-docosanol, tromantadine and idoxuridine;

Anthelmintics such as mebendazole, thiabendazole, niclosamide, praziquantel, pyrantel embonate and diethylcarbamazine;

Cytotoxic agents such as plicamycin, cyclophosphamide, dacarbazine, fluorouracil and its prodrugs (described, for example, in *International Journal of Pharmaceutics,* 111, 223-233 (1994)), methotrexate, procarbazine, 6-mercaptopurine and mucophenolic acid;

Anorectic and weight reducing agents including dexfenfluramine, fenfluramine, diethylpropion, mazindol and phentermine;

Agents used in hypercalcaemia such as calcitriol, dihydrotachysterol and their active derivatives or analogs;

Antitussives such as ethylmorphine, dextromethorphan and pholcodine;

Expectorants such as carbolcysteine, bromhexine, emetine, quanifesin, ipecacuanha and saponins;

Decongestants such as phenylephrine, phenylpropanolamine and pseudoephedrine;

Bronchospasm relaxants such as ephedrine, fenoterol, orciprenaline, rimiterol, salbutamol, sodium cromoglycate, cromoglycic acid and its prodrugs (described, for example, in *International Journal of Pharmaceutics* 7, 63-75 (1980)), terbutaline, ipratropium bromide, salmeterol and theophylline and theophylline derivatives;

Antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine;

Local anaesthetics such as benzocaine bupivacaine, amethocaine, lignocaine, lidocaine, cinchocaine, dibucaine, mepivacaine, prilocaine, etidocaine, veratridine (specific c-fiber blocker) and procaine;

Stratum corneum lipids, such as ceramides, cholesterol and free fatty acids, for improved skin barrier repair [Man, et al. *J. Invest. Dermatol.,* 106(5), 1096, (1996)];

Neuromuscular blocking agents such as suxamethonium, alcuronium, pancuronium, atracurium, gallamine, tubocurarine and vecuronium;

Smoking cessation agents such as nicotine, bupropion and ibogaine;

Insecticides and other pesticides which are suitable for local application;

Dermatological agents, such as vitamins A, C, B1, B2, B6, B12, B12α, and E, vitamin E acetate and vitamin E sorbate;

Allergens for desensitisation such as house, dust or mite allergens;

Nutritional agents and neutraceuticals, such as vitamins, essential amino acids and fats;

Macromolecular pharmacologically active agents such as proteins, enzymes, peptides, polysaccharides (such as cellulose, amylose, dextran, chitin), nucleic acids, cells, tissues, and the like;

Bone mending biochemicals such as calcium carbonate, calcium phosphate, hydroxyapetite or bone morphogenic protein (BMP);

Angiogenic growth factors such as Vascular Endothelial Growth Factor (VEGF) and epidermal growth factor (EFG), cytokines interleukins, fibroblasts and cytotaxic chemicals; and Keratolytics such as the alpha-hydroxy acids, glycolic acid and salicylic acid; and DNA, RNA or other oligonucleotides.

Additionally, the biomatrix materials of the present invention are particularly advantageous for the encapsulation, incorporation and/or scaffolding of macromolecular pharmacologically active agents such as proteins, enzymes, peptides, polysaccharides, nucleic acids, cells, tissues, and the like. Immobilization of macromolecular pharmacologically active agents into or onto a particle can be difficult due to the ease with which some of these macromolecular agents denature when exposed to organic solvents, some constituents present in bodily fluids or to temperatures appreciably higher than room temperature. However, since the method of the present invention utilizes biocompatible solvents such as water, DMSO or ethanol the risk of the denaturation of these types of materials is reduced. Furthermore, due to the size of these macromolecular pharmacologically active agents, these agents may be encapsulated within the biocompatible protein sleeves and particles and thereby are protected from constituents of bodily fluids that would otherwise denature them. Thus, the biomatrix materials of the present invention allow these macromolecular agents to exert their therapeutic effects, while yet protecting them from denaturation or other structural degradation.

Examples of cells which can be utilized as the pharmacologically active agent in the biomatrix material and/or biocompatible protein particles of the present invention include primary cultures as well as established cell lines, including transformed cells. Examples of these include, but are not limited to pancreatic islet cells, human foreskin fibroblasts, Chinese hamster ovary cells, beta cell insulomas, lymphoblastic leukemia cells, mouse 3T3 fibroblasts, dopamine secreting ventral mesencephalon cells, neuroblastold cells, adrenal medulla cells, endothelial cells, T-cells combinations of these, and the like. As can be seen from this partial list, cells of all types, including dermal, neural, blood, organ, stem, muscle, glandular, reproductive and immune system cells, as well as cells of all species of origin, can be encapsulated and/or delivered successfully by this method.

Examples of proteins which can be incorporated into the biomatrix material and/or biocompatible protein particles of the present invention include, but are not limited to, hemoglobin, vasporessin, oxytocin, adrenocorticocotrophic hormone, epidermal growth factor, prolactin, luliberin or luteinising hormone releasing factor, human growth factor, and the like; enzymes such as adenosine deaminase, superoxide dismutase, xanthine oxidase, and the like; enzyme systems; blood clotting factors; clot inhibitors or clot dissolving agents such as streptokinase and tissue plasminogen activator; antigens for immunization; hormones; polysaccharides such as heparin and rituximab; oligonucleotides; bacteria and other microbial microorganisms including viruses; monoclonal antibodies, such as herceptin; vitamins; cofactors; growth factors; retroviruses for gene therapy, combinations of these and the like.

An efficacious amount of the aforementioned pharmacologically active agent(s) can easily be determined by those of ordinary skill in the art taking into consideration such parameters as the particular pharmacologically active agent chosen, the size and weight of the patient, the desired therapeutic effect, the pharmacokinetics of the chosen pharmacologically active agent, and the like, as well as by reference to well known resources such as Physicians' Desk Reference®: PDR—52 ed (1998)—Medical Economics 1974. In consideration of these parameters, it has been found that a wide range exists in the amount of the pharmacologically active agent(s) capable of being incorporated into and subsequently released from or alternatively allowed to exert the agent's therapeutic effects from within, the biomatrix material and/or biocompatible protein particles. More specifically, the amount of pharmacologically active agent that may be incorporated into and then either released from or active from within the biomatrix material and/or biocompatible protein particles may range from about 0.001% to about 200%, more preferably, from about 0.05% to about 100%, most preferably from about 0.1% to 70%, based on the weight of the biomatrix material and/or biocompatible protein particles. It is important to note that the pharmacologically active agents are generally homogenously distributed throughout the biomatrix material and/or biocompatible protein particles thereby allowing for a controlled release of these agents.

Finally, one or more additive materials may be added to the biomatrix material to manipulate the material properties and thereby add additional structure or modify the release of pharmacologically active agents. That is, while a biomatrix material that includes a relatively fast-degrading protein material without a particular additive material will readily degrade thereby releasing drug relatively quickly upon insertion or implantation, a biomatrix material that includes a particular polymeric material, such as polyanhydride, will degrade slowly, as well as release the pharmacologically active agent(s) over a longer period of time. Examples of biodegradable and/or biocompatible additive materials suitable for use in the biomatrix materials utilized in the sleeves and/or particles of the present invention include, but are not limited to polyurethanes, vinyl homopolymers and copolymers, acrylate homopolymers and copolymers, polyethers, cellulosics, epoxies, polyesters, acrylics, nylons, silicones, polyanhydride, poly(ethylene terephthalate), polyacetal, poly (lactic acid), poly(ethylene oxide)/poly(butylene terephthalate) copolymer, polycarbonate, poly(tetrafluoroethylene) (PTFE), polycaprolactone, polyethylene oxide, polyethylene glycol, poly(vinyl chloride), polylactic acid, polyglycolic acid, polypropylene oxide, poly(akylene)glycol, polyoxyethylene, sebacic acid, polyvinyl alcohol (PVA), 2-hydroxyethyl methacrylate (HEMA), polymethyl methacrylate, 1,3-bis (carboxyphenoxy)propane, lipids, phosphatidylcholine, triglycerides, polyhydroxybutyrate (PHB), polyhydroxyvalerate (PHV), poly(ethylene oxide) (PEO), poly ortho esters, poly (amino acids), polycynoacrylates, polyphophazenes, polysulfone, polyamine, poly(amido amines), fibrin, graphite, flexible fluoropolymer, isobutyl-based, isopropyl styrene, vinyl pyrrolidone, cellulose acetate dibutyrate, silicone rubber, copolymers of these, and the like. Other materials that may be incorporated into the biomatrix material to provide enhanced features include, but are not limited to, ceramics, bioceramics, glasses bioglasses, glass-ceramics, resin cement, resin fill; more specifically, glass ionomer, hydroxyapatite, calcium sulfate, $Al_2O_3$, tricalcium phosphate, calcium phosphate salts, sugars, starches, carbohydrates, salts, polysaccharides, alginate and carbon. Additional other materials that may be incorporated into the biomatrix materials included alloys such as, cobalt-based, galvanic-based, stainless steel-based, titanium-based, zirconium oxide, zirconia, aluminum-based, vanadium-based, molybdenum-based, nickel-based, iron-based, or zinc-based (zinc phosphate, zinc polycarboxylate).

One method of producing the biomatrix materials is by providing one or more selected biocompatible proteins, adding other materials (pharmacologically active agents, additives, etc.) and solvents (water) to form a coatable composition. Once prepared, the coatable composition may be coated onto any suitable surface from which it may be released after drying by any suitable method. Examples of suitable coating techniques include spin coating, gravure coating, flow coating, spray coating, coating with a brush or roller, screen printing, knife coating, curtain coating, slide curtain coating, extrusion, squeegee coating, and the like. The coated film (preferably having a substantially planar body having opposed major surfaces) is desirably thin enough so as to be capable of drying within a reasonable amount of time and also thin enough so that the film can be formed into a cohesive body comprising a substantially homogeneous dispersion of the components of the coatable composition. For example, a thinner film will tend to form a more homogeneous cohesive body when the film is formed into the shape of a cylinder. A typical coated film of the coatable composition have a thickness in the range of from about 0.01 millimeters to about 5 millimeters, more preferably from about 0.05 millimeters to about 2 millimeters.

Initially, when the film is first coated, it is likely to be non-cohesive, fluidly-flowable, and/or non self-supporting. Thus, the coated film is preferably dried sufficiently so that it becomes cohesive, i.e., the film preferably sticks to itself rather than other materials. The film may simply be allowed to dry at room temperature, or alternatively, may be dried under vacuum, conditions of mild heating, i.e., heating to a temperature of from about 25° C. to about 150° C., or conditions of mild cooling, i.e. cooling to a temperature of from about 0° C. to about 20° C. When utilizing heat to dry the film, care should be taken to avoid denaturation or structural degradation of the pharmacologically active agent incorporated therein.

The specific solvent content at which the film becomes cohesive unto itself will depend on the individual components incorporated into the coatable composition. Generally, films that have too high of a solvent content will not be cohesive. Films that have too low of a solvent content will tend to crack, shatter, or otherwise break apart upon efforts to form them into a cohesive body. With these considerations in mind, the solvent content of a partially dried film will preferably be from about 10% to about 80%, more preferably from about 15% to about 65% and most preferably from about 20% to about 50%.

Once the film is capable of forming a cohesive body, such a cohesive body may be formed by any of a number of methods. For example, the film may be rolled, folded, accordion-pleated, crumpled, or otherwise shaped such that the resulting cohesive body has a surface area that is less than that of the coated film. For example the film can be shaped into a cylinder, a cube, a sphere or the like. Preferably, the cohesive body is formed by rolling the coated film to form a cylinder.

Once so formed, the cohesive body may be optionally compressed to form a biomatrix material. The biomatrix material may be formed into any number of shapes and sizes. For example to prepare the fixation sleeves of the present invention the biomatrix material may be formed into a sheet of the appropriate size to extend around and cover the injured part of the body, such as a fractured bone. Alternatively, the biomatrix material may be formed into a cylinder for subsequent pulverization into particles (an explanation of particle making is described below).

Any manually or automatically operable mechanical, pneumatic, hydraulic, or electrical molding device capable of subjecting the cohesive body to pressure is suitable for use in the method of the present invention. In the production of various embodiments of the present invention, a molding device may be utilized that is capable of applying a pressure of from about 100 pounds per square inch (psi) to about 100,000 psi for a time period of from about 2 seconds to about 48 hours. Preferably, the molding device used in the method of the present invention will be capable of applying a pressure of from about 1000 psi to about 30,000 psi for a time period of from about 10 seconds to about 60 minutes. More preferably, the molding device used in the method of the present invention will be capable of applying a pressure of from about 3,000 psi to about 25,000 psi for a time period of from about one minute to about ten minutes.

Compression molding devices suitable for use in the practice of the method of the present invention are generally known. Suitable devices may be manufactured by a number of vendors according to provided specifications, such as desirable pressure, desired materials for formulation, desired pressure source, desired size of the moldable and resulting molded device, and the like. For example, Gami Engineering, located in Mississauga, Ontario manufactures compression molding devices to specifications provided by the customer. Additionally, many compression molding devices are commercially available. See U.S. Pat. No. 6,342,250 and U.S. application Ser. No. 09/796,170, and U.S. Provisional Application Ser. No. 60/376,136, filed on Apr. 29, 2002, which are incorporated by reference herein, for a description of one type of compression molding device that may be utilized in the process of the present invention.

The compression molding devices utilized in the process of the present invention are generally capable of applying from about 100 psi to about 100,000 psi for a time period of from about 2 seconds to about 48 hours, preferably capable of applying from about 1000 psi to about 30,000 psi for a time period of from about 10 seconds to about 60 minutes, and more preferably, capable of applying a pressure of from about 3000 psi to about 25,000 psi for a time period of from about 1 minute to about 10 minutes.

The resulting biomatrix material preferably has as little solvent as possible while still being cohesive and possessing the desired features relevant to the device's function, e.g., preferably a solvent content of from about 5% to about 60%, more preferably a solvent content of from about 10% to about 50% and most preferably 20% to 40%. It is found that when a biomatrix material of the present invention includes one or more pharmacologically active agents; the partial drying of the film to form a cohesive body and subsequent compressing of the cohesive body, forces more solvent out of the body, thereby producing a resulting biomatrix material that has a significantly higher concentration of pharmacologically active agents relative to other components of the material. As a result of the substantially uniform dispersion of a greater concentration of pharmacologically active agent, a sustained, controlled release of the pharmacologically active agent is achieved, while reducing the initial high concentration effects that can be associated with other devices that include pharmacologically active agents.

The biocompatibility and tissue response to such biomatrix material has been shown to be favorable in related cardiovascular and drug delivery research. The biocompatibility of the protein matrix material has been demonstrated through several studies. In one study, cylindrical implants (3.5 mm×8 mm) were implanted next to the sciatic nerve in a rat model. The implants were left in place up to 12 weeks. The biomatrix material used in this study was designed to not react with any cells, but to demonstrate the surrounding tissue response to the material. The implants that were dissected and histological evaluations of the surrounding tissues were performed. The sections were stained with Masson's trichrome to highlight the connective tissue. A mild connective tissue formation around the implant was observed. The connective tissue around the implant serves to hold the implants in place. The amount of tissue observed at the 12 week time period was less than 20 microns compared to the several hundred microns that normally hold nerves in place. A histology slide from the sciatic nerve study is shown in FIG. 1.

Figure 2:
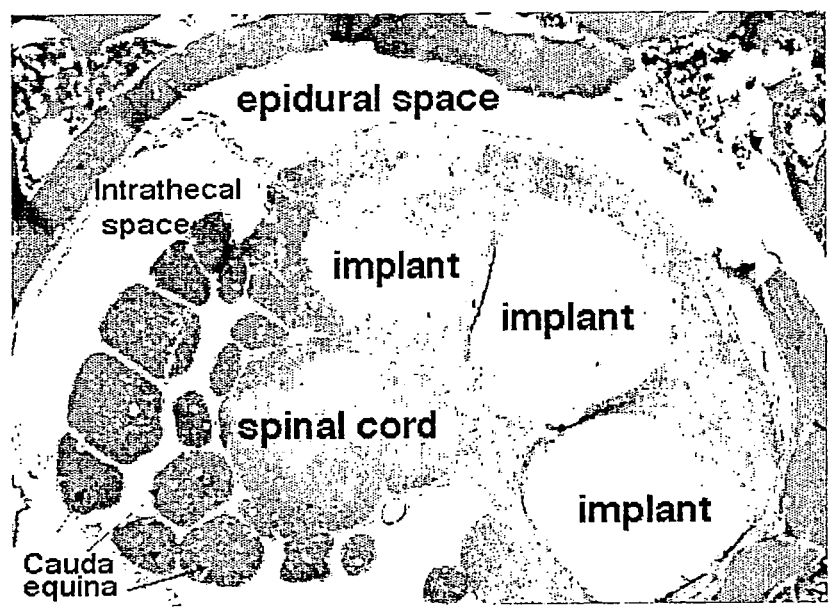
FIG. 2 depicts a histological image including an implant of one embodiment of the biomatrix material of the present invention.

A second study was conducted where 1 mg size biomatrix cylinders were implanted into the epidural space of rats at lumbar vertebrae 2. All implants were sterilized prior to implantation by means of gamma irradiation. This study showed that the implants could deliver an opiate drug for 10 days in vitro and caused an analgesic effect for 10 days in rats receiving these epidural implants. All rats returned to normal behavior and pre-baseline analgesic testing scores. Hind limb strength was also tested in these animals and no effects were observed for the entire course of study. The implants and the surrounding tissue underwent histological assessment after explanted. The sections were stained with H & E. A histological section from the study (2 weeks post implantation) is shown below in FIG. 2. The biomatrix materials were found to be biocompatible and demonstrate a favorable tissue response.

Many other biocompatibility studies have been completed. Subcutaneous implants in rats (3.5 mm i.d. 8 mm tong, n=6 per time point) at 1, 2, 4, 6, 8 and 12 weeks were evaluated histologically using H & E staining and Masson's trichrome staining. It was found that acute inflammatory reaction to the biomatrix implants resolved within 3±2 days and that chronic inflammatory reaction resolved in 7±4 days. There were only occassional giant cells observed in a small fraction of the rats for the 2, 4, 6 week time points. Many macrophages were observed penetrating the surface of the matrix as early as 1 week.

Figure 3:
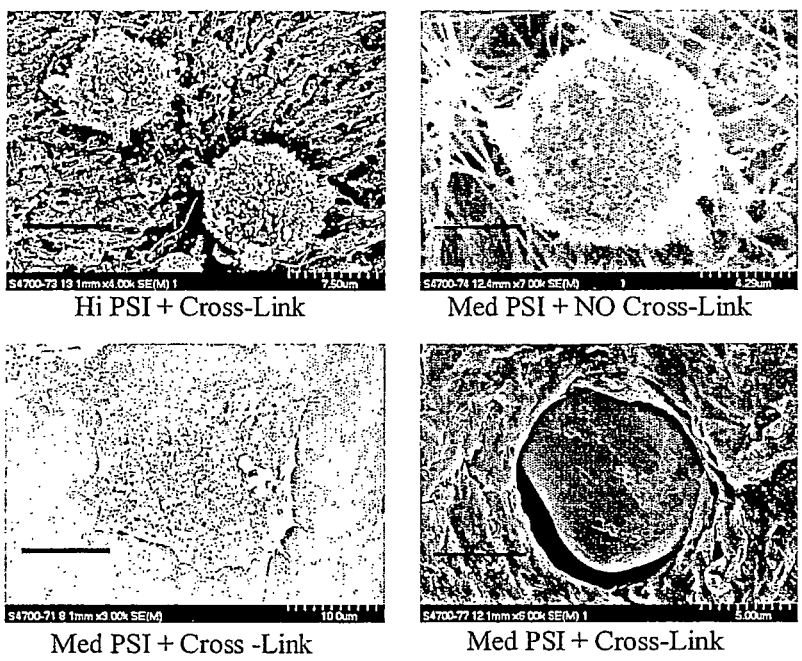
FIG. 3 depicts images of cell growth on one embodiment of the biomatrix material of the present invention.

The final area of research that is directly applicable to the present invention is the ability of cells to grow on the material. One study demonstrated this by showing fibroblasts attaching to various biomatrix embodiments containing collagen and elastin proteins. A sample of the study results are shown below in FIG. 3 (The bar in each quadrant is 7.5, 4.3, 10.0 and 5.0 pm shown in top left, top right, lower left and lower right figures, respectively).

The activity of an attached cell such as these fibroblasts can be altered by changes in the fabrication technique (compression & cross-linking) and composition of the biomatrix materials. Additionally, cells can take on different shapes depending upon the type of biomatrix material they contact. The ability of cells to take on different shapes is indicative of their ability to respond to their environment for specialized cell functions (e.g., differentiation, proliferation).

The combined preliminary work aimed at the processing, the biocompatibility, the drug release, and the cell attachment capabilities demonstrate that the containment sleeve and particles of the present invention can be applied as materials for numerous clinical applications including many areas of orthopaedic surgery for bone and cartilage repair.

The processing of the material can be tailored for many specific applications and forms. For application to orthopedic products, a composite material can be generated. For example, the composite may include a base protein matrix including hydroxyapatite and collagen. However, it is noted that other proteins and/or biocompatible materials, such as minerals and pharmacologically active agents may be utilized in base protein matrix. The composite matrix material may then be processed into the fixation system of the present invention comprising a containment sleeve and/or particles.

As previously suggested, embodiments of the fixation device of the present invention may utilize two constructs of the biomatrix material, sheets and particles. These two constructs can be utilized as a fixation device either separately or in concert with each other. A number of embodiments of the first construct include a sheet form of the biomatrix material which may be further formed into a containment and fixation sleeve. In various embodiments of the present invention, sheets, as previously proposed, may be manufactured using a compression molding process while controlling the input materials to make a sheet of a defined thickness and consistent structure. The sheets utilized may be of any thickness. However, sheets generally range from 0.01-50 mm thick and preferably 0.20-10 mm thick.

The biomatrix sheets utilized in the containment sleeve of some embodiments of the present invention may include one or more sides that are crosslinked to provide additional beneficial characteristics and one or more sheets can be incorporated together in a laminar form. Crosslinking of the sleeve may be performed by any means known in the art such as exposure to chemical crosslinking agents like glutaraldehyde, p-Azidobenzolyl Hydazide, N-5-Azido 2-nitrobenzoyloxysuccinimide, N-Succinimidyl 6-[4'azido-2'nitro-phenylamino]hexanoate and 4-[p-Azidosalicylamido]butylamine, ultraviolet light or other radiation sources like ultrasound or gamma rays.

Figure 4:
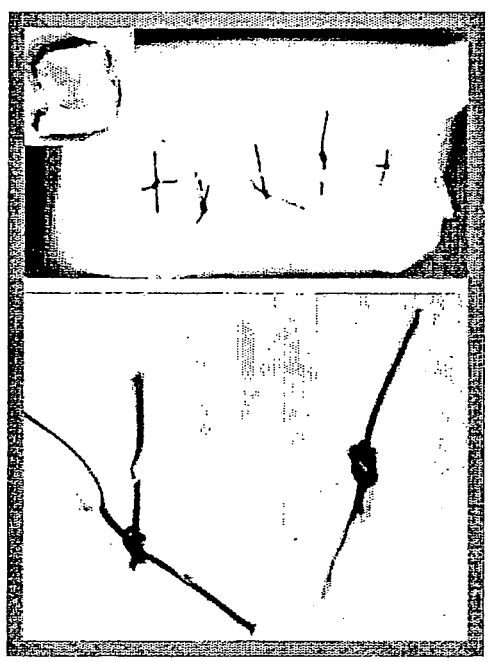
FIG. 4 depicts one embodiment of the containment sleeve of the present invention comprising a biomatrix material that is fastened with sutures.

FIG. 4 depicts one embodiment of the containment sleeve of the present invention. This embodiment of the present invention includes one or more sheets of the biomatrix material made from collagen-elastin proteins. It is noted that two or more sheets of different material may be utilized as a laminate to provide the attributes desired depending on the injury. The sheet or sheets can be fastened together at the ends with various suitable fastening devices, such as adhesives, staples, cerclages, screws, plates and/or sutures so as to create an enclosure, such as a tube or hollowed block. The adhered ends of the sheet may butt up to each other or be overlapped during fastening. The embodiment in FIG. 4 illustrates how well nylon suture can be used to hold the sheets together in a tubular assembly.

Further studies with the biomatrix material shows that the material is permeable to small solutes and solutions but does not leak fluid even around suture holes. The biomatrix material has been shown to be quite elastic and strong (>50% elasticity possible in mechanical testing with over 5 psi ultimate tensile strength in 0.2 mm thick material).

Figure 5:
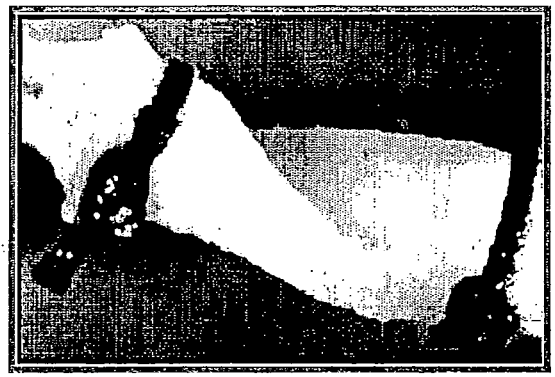
FIG. 5 depicts the elasticity of one embodiment of the containment sleeve of the present invention comprising a biomatrix material.

FIG. 5 depicts another embodiment of containment sleeve which includes the biomatrix material. The sleeve illustrated in FIG. 5 (approximately 0.2 mm thick) was centered over the ends of polyethylene tubing and fixed with glue and clamped down with silk suture. The material was then tested for strength and flexibility. It was found that the containment sleeve of this embodiment was quite compliant, strong and flexible. This test and subsequent tests showed that ultimate tensile strength exceeded 10 psi and that the material was >50% elastic without losing strength.

Two specific embodiments of the composition are generally comprised of hydroxyapatite and a protein or proteoglycan such as collagen or collagen-elastin-heparin. The first includes 10-20% hydroxyapatite, preferably 15% hydroxyapatite by weight and the second includes 25-35% hydroxyapatite, preferably 30% hydroxyapatite by weight. However, hydroxyapatite can be incorporated in higher or lower amounts ranging 0%-75% by weight and preferably from 10%-40% by weight.

As previously suggested the biomatrix material is formed into a sheet and is capable of being placed around a fractured bone. For example sheets made of polyurethane, polytetrafluoroethylene, polyvinylalcohol, polylactic acid or any other biocompatible material may be formed into a sleeve that may be utilized in the fixation device of the present invention.

It is noted that the material utilized to prepare the containment sleeve of the present invention may be comprised of any biocompatible polymeric material, including but not limited to proteins. Furthermore the biocompatible polymeric material may include pharmacologically active agents, which are delivered to the injured or diseased site.

The containment sleeve of the present invention may be produced to remodel with and/or resorb into the surrounding tissue or remain positioned around the fractured area after it has mended. Also, the containment sleeve may function by itself or in cooperation with the particles described below.

In operation of one embodiment of the present invention, a fracture fixation sleeve is constructed from a sheet formed to proper dimensions or cut to size from a sheet of biomatrix material; for example a sheet made with hydroxyapatite and collagen. However, as previously mentioned a sheet comprised of any biocompatible material may be utilized. Once the biomatrix material is available in a sheet of proper size and shape, it can be positioned around the fracture area or other injured area, such as a nerve fractured or damaged area like the spinal cord to function as a containment sleeve for delivery of therapeutic biochemicals or containment from undesirable components of the body. As previously noted, other biochemicals and/or pharmacologically active agents may be utilized in the present invention. The sleeve may be secured by a variety of fastening devices, including but not limited to, staples, cerclages, screws, plates, adhesives, bindings and/or any other suitable fasteners for holding the sleeve in place around the fracture site. It is noted that the staples, cerclages, screws, plates, adhesives, bindings and/or any other suitable fasteners may also be made of a biomatrix material of sufficient strength and rigidity to penetrate the sleeve material and/or fractured bone to secure the sleeve in place. Once the containment sleeve is placed into position over the injured site, it can provide therapeutic relief to the injury and promote proper healing. It is noted that the containment and fixation sleeve of the present invention may also be utilized for implanted prosthetic device implantation, such as the implantation of knee and hip prosthetics. The containment sleeve can be of assistance in prosthetic implantation to contain wear debris and to facilitate integration of the surrounding bone and tissue (e.g. cartiledge and bone integration) with the prosthetic device.

Figure 6:
FIG. 6 depicts particles of the present invention which include the biomatrix material.

The fixation device of the present invention may also comprise the biomatrix material constructed into particles of any size. An illustration of an embodiment of the particles of the present invention is depicted in FIG. 6. In one, embodiment of the present invention the particles are produced utilizing the biomatrix material previously described. Alternatively, particles may be derived from a biocompatible protein material produced by applying heat, freeze drying techniques such as liquid nitrogen or dry ice freeze drying, vacuum or other similar drying techniques to eliminate excess solvent from the cohesive body rather than compressing it. These alternative techniques remove enough solvent from the cohesive body to provide for the production of distinct particles, but do not eliminate too much solvent wherein the interaction of solvent and protein is lost. Generally, many particle embodiments of the present invention are substantially insoluable thereby allowing them to be integrated and remodeled by the host tissue rather than be consumed and excreted.

One example of an alternative method to make particles is by heating the cohesive body and then processing the resulting cohesive body into particles. In such a method the cohesive body may be heated at temperatures ranging from 0°-150° C., preferably 20°-1.20° C. and most preferably 40°-100° C. Generally, the heating process may be conducted for approximately 5 minutes to 48 hours, preferably 1-24 hours and most preferably 2-6 hours. Embodiments of the resulting cohesive body following heating, or any of the alternative techniques identified above, usually have as little solvent as possible while still being cohesive and possessing the desired features relevant to the device's function, e.g., preferably a solvent content of from about 5% to about 60%, more preferably a solvent content of from about 10% to about 50% and most preferably 20% to 40%.

Before the biomatrix material or biocompatible protein material is processed into particles it may also be crosslinked to provide additional beneficial characteristics. The optional step of crosslinking the biomatrix material or biocompatible protein material may be performed by any means known in the art such as exposure to chemical crosslinking agents like glutaraldehyde, p-Azidobenzolyl Hydazide, N-5-Azido 2-nitrobenzoyloxysuccinimide, N-Succinimidyl 6-[4'azido-2'nitro-phenylamino]hexanoate and 4-[p-Azidosalicylamido]butylamine, ultraviolet light or other radiation sources like ultrasound or gamma ray.

The particles of the present invention are generally prepared by further processing the biomatrix material or biocompatible protein material produced by the alternative methods described above. FIG. 6 depicts embodiments of the biocompatible protein particles of the present invention. One method of producing the particles utilized in products of the present invention includes the crushing, cutting, pulverizing or grinding of the biomatrix material and/or biocompatible protein material.

Generally, the particles may vary in size but are normally approximately 10 nm-5 mm, preferably 500 nm-2.5 mm and more preferably 1-1000 um. A characteristic of the particles produced from the biocompatible protein material is that they no longer aggregate when in the particulate state. Furthermore, prior studies have demonstrated that the particles do not aggregate in saline and are easily delivered through small gauge needles. The particles can be made to disassociate at very slow or fast rates in aqueous solutions.

After the particles are formed using the various methods described above, they are characterized for their basic structure. First the particles may be segregated using a series of pharmaceutical drug sieves. Additional characterization of the particles will consist of verification of the shape and size of the particles using light and electron microscopy (FIG. 6).

The particles may be utilized as a fixation device by administering them to the fractured bone or other fractured site such as the spinal cord by a variety of administration techniques. Various embodiments of the present invention include the ability to incorporate both hydroxyapatite and collagen into the particles of the present invention, which are administered to the fracture site. One administration procedure of the present invention includes the injection of the particles in a slurry into the injured site by syringe. This procedure provides for the particles being placed in solution for delivery. Saline is a solution that may be employed to prepare the slurry, but any biocompatible solution may be utilized. Saline has been selected for the initial material for several reasons including its common use in medical procedures and its availability in a sterile form. The slurry may be delivered in any way known in the art including delivery through a needle. Any gauge needle may be utilized to deliver the slurry containing the particles of the present invention, including but not limited to 12-26 gauge needles.

Alternatively, the particles of the present invention may also be placed into position without utilizing needles, such as when the particles are too large to fit through a needle. These particles are typically 0.5-5 mm in size, more typically 1-25 mm. In such a procedure the particles may be surgically implanted and packed into and/or around the injured site. For example, particles may be surgically packed into and around a bone fracture and subsequently sealed into position by the host tissue surrounding the fractured bone.

Finally, an additional embodiment of the fixation device of the present invention includes the utilization of both the containment sleeve and the particles. The method to use the fixation system of the present invention at an injury or deterioration site, such as a fracture generally comprises positioning the containment sleeve completely or partially around the fracture site. Next, either 1) particles are placed in the sleeve and the sleeve is secured into position; or 2) the sleeve is secured and particles or a particle slurry is injected into the secured sleeve. As previously mentioned, a series of fixation devices including sutures, cerclages, staples, adhesives, plates, screws, bindings, bands and any other fasteners may be utilized to attach the sheet of biomatrix material thereby wrapping around the bone ends to make a tube or other shaped enclosure. The biomatrix enclosure or containment sleeve acts to contain healing bone particles, such as the particles of the present invention, bone fragments, or the like, within the tube. The biomatrix enclosure or containment sleeve also acts to maintain the beneficial healing components generated by the bone site within the site and further keeps detrimental components (e.g. soft tissue and/or inflammatory cells) that may inhibit healing out of the site. As previously indicated, additional drugs or bone enhancing growth factors (e.g. bone morphogenic protein, BMP) may be incorporated into the biomatrix material of the containment sleeve and/or particles that will increase the rate of bone and tissue growth and bone and tissue healing, enhance cell attachment and reduce pain.

In another embodiment of the present invention, the implant system comprises a fracture fixation sleeve constructed from a sheet cut to size from a sheet of biomatrix material, for example a sheet made with hydroxyapatite and collagen/elastin or hydroxyapatite and collagen-elastin-heparin. Once produced, the hydroxyapatite and protein matrix sleeve is wrapped around a fracture site and secured into place. The sleeve may be secured by a variety of fastening devices, including but not limited to, staples, cerclages, screws, plates, adhesives, bindings, sutures and/or any other suitable fasteners for holding the sleeve in place around the fracture site. It is noted that the staples, cerclages, screws, plates, adhesives, bindings and/or any other suitable fasteners may also be made of a biomatrix material of sufficient strength and rigidity to penetrate the sleeve material and/or fractured bone to secure the sleeve in place. Particles fashioned from the biomatrix material or biocompatible protein are then injected and/or placed into the sleeve. It is noted that alternatively the particles of the present invention may be packed in or around the fracture site before the containment sleeve is administered to the site. The particles in conjunction with the sleeve enables bone to heal across defects through osteoconductive regeneration of bone tissue directed and contained by the sleeve and induced by the particles.

Figure 7:
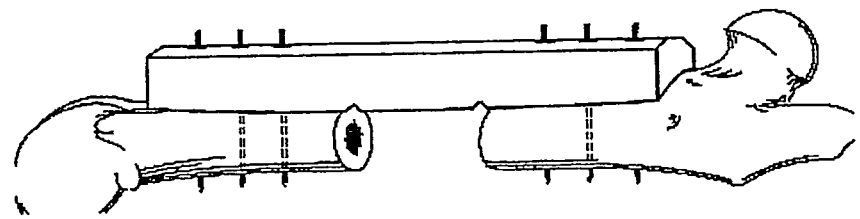
FIG. 7 depicts an image of a bone non-union defect model.

An illustration of utilizing the fracture fixation system of the present invention would be in the repair of a full-thickness segmental defect as depicted in the animal model of FIG. 7. The defect is stabilized under aseptic conditions with a polyacetyl plate and Kirchner wires. The animal model is based off of a study conducted previously by the MMRF Orthopaedic Biomechanics Lab.

Figure 8:
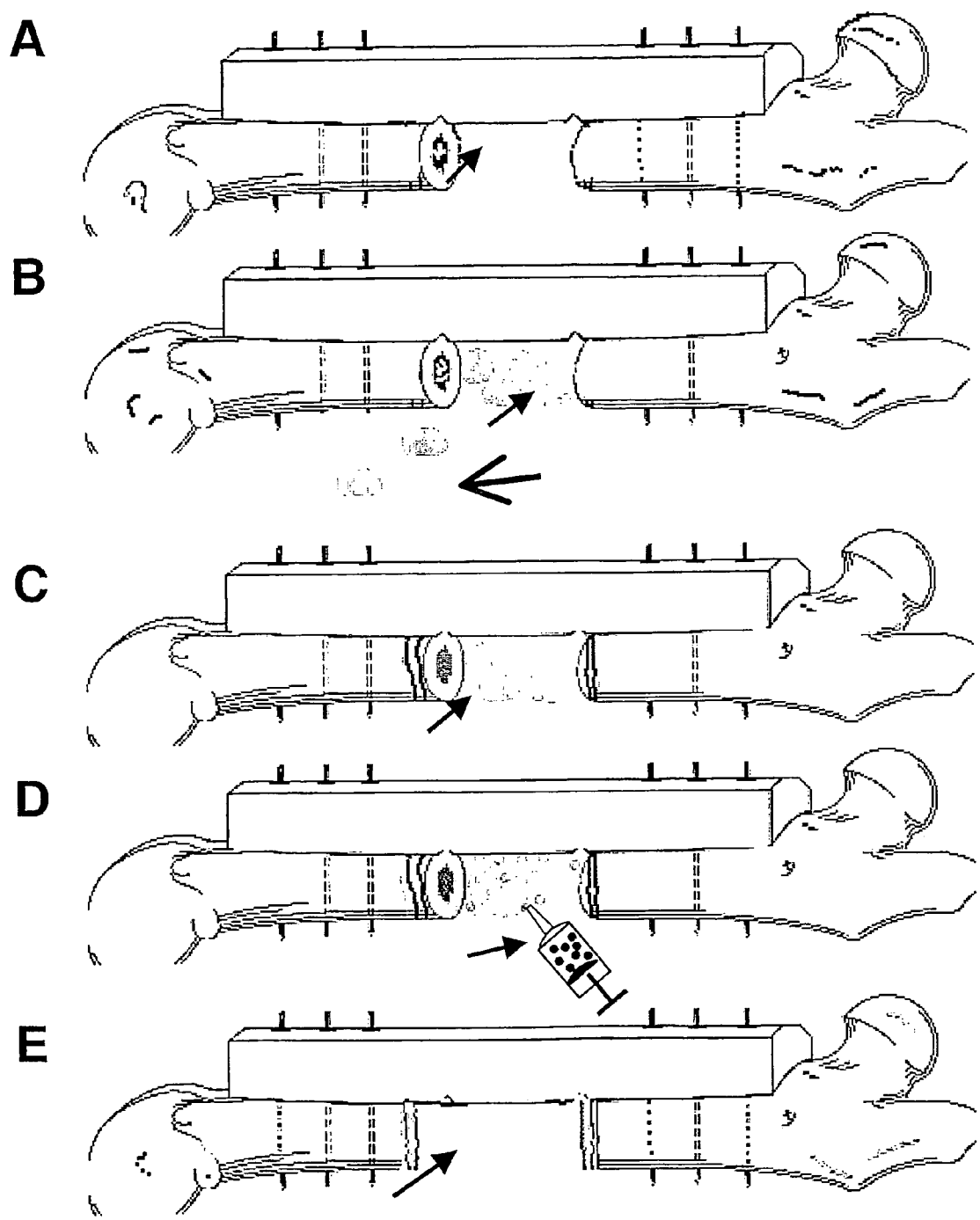
FIG. 8 depicts a process for administering the containment and fixation system of the present invention to a bone non-union defect.

In treating such a segmental defect model as depicted in FIG. 7, an embodiment of the fixation system of the present invention may be administered to provide assistance in the mending of the fracture. FIG. 8 illustrates the process of administering the fixation system of the present invention to a defect similar to the defect depicted in FIG. 7.

In FIG. 8 the defect includes a non-union fracture (A). Large particles are packed in and around the fracture (B). Next, a containment and fixation sleeve of the present invention, transparent for schematic, is wrapped around the fracture and banded to the bone with sutures (C). Following banding of the containment sleeve to the bone, a slurry of particles is injected inside the containment sleeve, transparent for schematic (D). Finally, the containment sleeve is sealed and secured around the around bone fracture by adhereing the ends of the containment sleeve to themselves (E).

While the invention has been described in conjunction with specific embodiments thereof, it variations, which fall within the spirit and broad scope of the invention.

The invention claimed is:
1. A biomatrix containment and fixation system comprising
 a containment and fixation sleeve including one or more sheet(s) of biomatrix material, the one or more of the sheet(s) having one or more biocompatible proteins combined with one or more biocompatible solvents to form a cohesive body having a solvent content of about 10% to 80% by weight prior to compression, the cohesive body is compressed at a pressure of about 100 psi to about 100,000 psi to form the sheet(s) of biomatrix material having a solvent content of about 5% to 60% by weight, said sleeve having two or more ends adhered together with one or more fastening device(s) to form an enclosure; and
 a plurality of protein particles positioned within the enclosure of the sleeve, said protein particles including one or more biocompatible proteins combined with one or more biocompatible solvents and one or more pharmacologically active agents.
2. The biomatrix containment and fixation system of claim 1 wherein the biocompatible proteins are selected from the group consisting of elastin, collagen, albumin, ovalbumin, keratin, fibronectin, silk, silk fibroin, actin, myosin, fibrinogen, thrombin, aprotinin, antithrombin III, genetically engineered proteins including blocks of peptide sequences comprising groups of amino acids, collagen-heparin, collagen-elastin-albumin-heparin, collagen-albumin, collagen-elastin-heparin and collagen-chondroitin.
3. The biomatrix containment and fixation system of claim 1 wherein the biocompatible solvent is selected from the group consisting of water, dimethyl sulfoxide (DMSO), biocompatible alcohols, biocompatible acids, oils and biocompatible glycols.
4. The biomatrix containment and fixation system of claim 1 wherein the sleeve includes one or more pharmacologically active agents and the one or more pharmacologically active agents included in the sleeve or in the sleeve and particles are selected from the group consisting of analgesics, anesthetics, antipsychotic agents, angiogenic growth factors, bone mending biochemicals, steroids, antiglacoma agents, antialcohol agents, anti-coagulants agents, genetic material, antithrombolytic agents, anticancer agents, anti-Parkinson agents, anti-epileptic agents, anti-inflammatory agents, anticonception agents, enzymes, cells, growth factors, antiviral agents, antibacterial agents, antifungal agents, hypoglycemic agents, antihistamine agents, chemoattractants, neutraceuticals, anti-obesity, smoking cessation agents, obstetric agents and antiasmatic agents.

5. The biomatrix containment and fixation system of claim 4 wherein the pharmacologically active agents are hydroxyapatite, bone morphogenic protein VEGF or combinations thereof.

6. The biomatrix containment and fixation system of claim 1 wherein the fastening device is one or more devices selected from the group consisting of staples, cerclages, screws, plates, adhesives and sutures.

7. The biomatrix containment and fixation system of claim 1, wherein the sleeve, particles or both further comprise one or more biocompatible additives.

8. The biomatrix containment and fixation system of claim 7 wherein the one or more biocompatible additives are selected from the group consisting of epoxies, polyesters, acrylics, nylons, silicones, polyanhydride, polyurethane, polycarbonate, poly(tetrafluoroethylene), polyethylene glycol, poly(vinyl chloride), polypropylene oxide, poly(akylene)glycol, polyoxyethylene, sebacic acid, polyvinyl alcohol, 2-hydroxyethyl methacrylate, polymethyl methacrylate, 1,3-bis(carboxyphenoxy)propane, lipids, polyhydroxybutyrate, polyhydroxyvalerate, poly (amino acids), polycyanoacrylates, polyphophazenes, polysulfone, polyamine, poly (amido amines), fibrin, graphite, flexible fluoropolymer, isobutyl-based, isopropyl styrene, vinyl pyrrolidone, cellulose acetate dibutyrate, silicone rubber, and copolymers of these.

9. The biomatrix containment and fixation system of claim 1 wherein all or a portion of the sleeve and particles are crosslinked with one or more crosslinking agents.

10. The biomatrix containment and fixation system of claim 9 wherein the one or more crosslinking agents are selected from the group consisting of glutaraldehyde, p-Azidobenzolyl Hydazide, N-5-Azido 2-nitrobenzoyloxysuccinimide, N-Succinimidyl 6-[4'azido-2'nitro-phenylamino]hexanoate and 4-[p-Azidosalicylamido]butylamine.

11. The biomatrix containment and fixation system of claim 1 wherein the particles have a size of approximately 10 nm to 5 mm.

12. The biomatrix containment and fixation system of claim 2 wherein the biocompatible proteins include collagen.

13. The biomatrix containment and fixation system of claim 2 wherein the biocompatible proteins include collagen and elastin.

14. The biomatrix containment and fixation system of claim 3 wherein the biocompatible solvent includes water.

15. The biomatrix containment and fixation system of claim 10 wherein the one or more crosslinking agents includes glutaraldehyde.

16. The biomatrix containment and fixation system of claim 1 wherein the sleeve and particles are formed from a cohesive body including the one or more biocompatible proteins, the one or more biocompatible solvents and optionally the one or more pharmacologically active agents.

17. The biomatrix containment and fixation system of claim 1, wherein the fastening device to form an enclosure includes staples, adhesives or sutures.

18. The biomatrix containment and fixation system of claim 1 wherein the fastening device includes one or more bindings.

19. The biomatrix containment and fixation system of claim 1 wherein the particles are formed from one or more cohesive bodies for particle preparation including one or more biocompatible proteins, one or more biocompatible solvents and one or more pharmacologically active agents, wherein the solvent content for each cohesive body for particle preparation is reduced from about 10% to 80% to about 5% to 60% by one or more techniques selected from the group consisting of compression, freeze drying, vacuum and heating, and wherein the solvent reduced cohesive bodies are further processed into the particles that are administered to the enclosure of the sleeve.

* * * * *